United States Patent
Venet et al.

(10) Patent No.: US 12,294,834 B2
(45) Date of Patent: May 6, 2025

(54) COCHLEAR IMPLANT SYSTEM WITH ANTENNA DETECTION, FREQUENCY SWITCHING AND/OR FREQUENCY TUNING

(71) Applicant: Cochlear Limited, Macquarie University (AU)

(72) Inventors: Julien Venet, Vallauris (FR); Philippe Monier, Vallauris (FR); Regis Pierquin, Vallauris (FR); Martin Besnard, Vallauris (FR)

(73) Assignee: Cochlear Limited, Macquarie University (AU)

( * ) Notice: Subject to any disclaimer, the term of this patent is extended or adjusted under 35 U.S.C. 154(b) by 230 days.

(21) Appl. No.: 18/075,796

(22) Filed: Dec. 6, 2022

(65) Prior Publication Data

US 2023/0179930 A1    Jun. 8, 2023

(30) Foreign Application Priority Data

Dec. 7, 2021  (EP) .................................. 21212770

(51) Int. Cl.
*H04R 25/00* (2006.01)
*A61N 1/36* (2006.01)

(52) U.S. Cl.
CPC ....... *H04R 25/505* (2013.01); *A61N 1/36038* (2017.08); *H04R 25/606* (2013.01); *H04R 2225/67* (2013.01)

(58) Field of Classification Search
CPC .............. H04R 25/505; H04R 25/606; H04R 2225/67; A61N 1/36038; A61N 1/37223
See application file for complete search history.

(56) References Cited

U.S. PATENT DOCUMENTS 6,175,767 B1   1/2001  Doyle, Sr.
9,166,655 B2  10/2015  Meskens et al.
(Continued)

FOREIGN PATENT DOCUMENTS

WO   WO 2021/038297 A1   3/2021

*Primary Examiner* — Tuan D Nguyen
(74) *Attorney, Agent, or Firm* — Edell, Shapiro & Finnan, LLC

(57) ABSTRACT

According to a first aspect, a sound processor unit of a cochlear implant system is disclosed. The sound processor unit comprises an electric circuit, which comprises a sound processor antenna with a sound processor antenna capacitance and a sound processor antenna inductance, wherein the sound processor antenna capacitance and the sound processor antenna inductance are connected in series and form a resonant circuit. An improved cochlear implant system is provided in that the electric circuit of the sound processor unit further comprises a switching element connected in series with the sound processor antenna capacitance and the sound processor antenna inductance, and the electric circuit of the sound processor unit further comprises an inductive element connected in parallel with the switching element, wherein when the switching element is in a closed state, the inductive element is in a short-circuited state and the sound processor antenna has a first resonant frequency, and when the switching element is in an open state, the inductive element is in a non-short-circuited state and the sound processor antenna has a second resonant frequency which differs from the first resonant frequency.

20 Claims, 7 Drawing Sheets

(56) References Cited

U.S. PATENT DOCUMENTS

2011/0046730 A1* 2/2011 Meskens ............ A61N 1/36038
607/55
2019/0074585 A1 3/2019 Vavelin et al.
2021/0170173 A1* 6/2021 Besnard ............... H04R 25/505

* cited by examiner

COCHLEAR IMPLANT SYSTEM WITH ANTENNA DETECTION, FREQUENCY SWITCHING AND/OR FREQUENCY TUNING

FIELD

The present disclosure relates to the field of hearing aid systems. More particularly, the disclosure relates to a cochlear implant system. Specifically, the disclosed aspects allow for antenna detection, frequency switching and/or frequency tuning.

BACKGROUND

A cochlear implant system is a hearing prosthesis for deaf people whose auditory nerve is still functionally, as well as for highly hearing-impaired people for whom a conventional hearing aid does not provide sufficient audio perception. The general principle of a cochlear implant system is to bypass the normal acoustic hearing process and to replace it with electric signals which directly stimulate the cochlear nerve. For this purpose, a cochlear implant system generally comprises two main components: a sound processor unit and an implant unit. The sound processor unit may be worn behind the ear or alternatively attached to clothing, for example. It may comprise microphones, a power supply, electronics and a sound processor antenna with a first magnet. The implant unit may comprise an implant unit antenna with a second magnet, electronics and an array of electrodes. It is surgically implanted such that the implant unit antenna is placed under the skin in the vicinity of the ear and the array of electrodes is placed in the cochlea to stimulate the cochlear nerve. By means of the magnets, the sound processor antenna of the sound processor unit adheres on the skin above the implant unit antenna of the implant unit. Both the power supply of the implant unit and the signal transmission between the sound processor unit and the implant unit happen transcutaneously, i.e. penetrating the skin, by means of electromagnetic induction. For this purpose, an inductive link may be established between the sound processor antenna and the implant unit antenna. For signal transmission, the technique of modulation can be used, where a carrier signal with a carrier frequency is modulated by the information signal to be transmitted.

A problem with cochlear implant systems of prior art is that it is difficult to adjust the sound processor unit for optimal audio perception by the user. This is because the mutual inductance of the sound processor antenna and the implant unit antenna is not universally constant. For example, the mutual inductance may vary because of different skin thicknesses of different users, different magnetic strengths, antenna misalignment, different lengths of antenna cords, or different power required by the user. The varying mutual inductance typically leads to the user having to select, from a set of sound processor antennas, a suitable sound processor antenna that matches their skin thickness. Furthermore, it can lead to disturbed communication between the sound processor unit and the implant unit, or complex algorithms having to be performed by the electronics to find the correct configuration for the user.

In addition, even when a suitable sound processor antenna has been selected, it is hard to optimise the inductive link between the sound processor antenna and the implant antenna for all conditions. This is because the conditions which the inductive link has to conform to may vary, for example due to varying skin thickness, different magnetic strengths, antenna misalignment, different lengths of antenna cords, or different power required by the user. Usually, a compromise for operating the inductive link must be found between efficiency of power transfer, complexity, cost, reliability and usability.

Another problem with cochlear implant systems of prior art is that the sound processor antenna may be disconnected from the sound processor unit, for example to replace the sound processor antenna by a different sound processor antenna. Therefore, when a connection between a sound processor antenna and the sound processor unit has been established, it is often required to quickly determine characteristics of the sound processor antenna, for example in order to establish the inductive link between the sound processor antenna and an implant antenna. In addition, it is desired to detect a state where no sound processor antenna is connected to the sound processor unit, for example in order to save power by putting the sound processor unit or components of the sound processor unit into a stand-by mode.

Therefore, there is a need to provide a solution that addresses at least some of the above-mentioned problems. The present disclosure provides at least an alternative to the prior art.

SUMMARY

According to a first aspect, a sound processor unit of a cochlear implant system is disclosed. The sound processor unit may comprise an electric circuit, which may comprise a sound processor antenna with a sound processor antenna capacitance and a sound processor antenna inductance. The sound processor antenna of the sound processor unit with the sound processor antenna capacitance and the sound processor antenna inductance allows the sound processor unit to transmit and/or receive signals, for example to and/or from an implant unit which may be inductively linked to the sound processor unit, as well as to transfer electric power to the inductively linked implant unit.

The sound processor antenna capacitance and the sound processor antenna inductance may be connected in series and form a resonant circuit. This allows the sound processor antenna to emit and/or absorb electromagnetic waves for transmitting and/or receiving signals, as well as to transfer electric power.

The electric circuit of the sound processor unit may further comprise a switching element connected in series with the sound processor antenna capacitance and the sound processor antenna inductance. The electric circuit of the sound processor unit may further comprise an inductive element connected in parallel with the switching element. When the switching element is in a closed state, the inductive element may be in a short-circuited state and the sound processor antenna may have a first resonant frequency. When the switching element is in an open state, the inductive element may be in a non-short-circuited state and the sound processor antenna may have a second resonant frequency which differs from the first resonant frequency. In this context, the closed state of the switching element is to be understood as a state in which an electric current flow over the switching element is enabled. The open state of the switching element is to be understood as a state in which an electric current flow over the switching element is interrupted.

By transitioning the switching element between the closed state and the open state, it is therefore possible, with the inductive element switching correspondingly between the short-circuited state and the non-short-circuited state, to switch the resonant frequency of the sound processor antenna between the first and the second resonance frequency. This allows the same type of sound processor unit to adapt to different resonant frequencies of an implant unit, for example. More specifically, an implant unit may have an implant antenna with a first resonant frequency that may be used when the skin thickness of the user is within a first interval, for example 1 mm to 6 mm. The implant antenna may have a second resonant frequency that may be used when the skin thickness is within a second interval, for example above 6 mm. By the sound processor unit being able to switch the resonant frequency of the sound processor antenna between the first and the second resonant frequency of the implant antenna, it is possible that the sound processor unit can establish an inductive link using different resonance frequencies corresponding to different skin thicknesses without having to exchange the sound processor antenna or the implant antenna. The user then no longer has to select a suitable sound processor antenna that matches their skin thickness from a set of sound processor antennas, such that user convenience is improved.

The switching element may comprise at least two transistors for short circuiting the inductive element. Thereby, a cost-effective, yet reliable switching element can be provided without numerous electronic components being required. However, a minimum of two transistors are needed as the current flowing through the transistors is sinusoidal and flows in both directions (quadratic behaviour).

The switching element may comprise at least a third transistor for controlling the at least two transistors that are used to short circuit the inductive element. Thereby, it is possible to simultaneously control the at least two transistors that can short circuit the inductive element.

The transistors of the switching element may be MOS transistors. By using MOS transistors for the switching element, the high space requirements of cochlear implant systems can be fulfilled better than for example with bipolar transistors, which is due to the MOS transistors being more suitable for miniaturisation. Furthermore, MOS transistors are advantageous in that they are easy to control due to their saturation state and in that they have a low power loss.

The switching element may comprise a DC voltage supply, a first NMOS transistor, a second NMOS transistor, a PMOS transistor, a first resistor and a second resistor. The DC voltage supply may comprise a positive terminal and a negative terminal. The first and second NMOS transistor and the PMOS transistor may comprise in each case a gate connection, a source connection and a drain connection. The first and second resistor may comprise in each case a first end connection and a second end connection. The negative terminal of the DC voltage supply may be electrically conductively connected to ground. The positive terminal of the DC voltage supply may be electrically conductively connected to the source connection of the PMOS transistor. The drain connection of the PMOS transistor may be electrically conductively connected to the first end connection of the first resistor, to the first end connection of the second resistor, to the gate connection of the first NMOS transistor, and to the gate connection of the second NMOS transistor. The source connection of the first NMOS transistor may be electrically conductively connected to the source connection of the second NMOS transistor. The second end connection of the first resistor may be electrically conductively connected to the drain connection of the first NMOS transistor. The second end connection of the second resistor may be electrically conductively connected to the drain connection of the second NMOS transistor. The switching element comprising a DC voltage supply, a first NMOS transistor, a second NMOS transistor, a PMOS transistor, a first resistor and a second resistor, which are electrically conductively connected to one another and to ground as explained above, may be a particularly advantageous realization. More specifically, the switching element is adapted to a sinusoidal wave form of the current and easily controllable from a digital sound processor of the sound processor unit, which may be electrically conductively connected to the gate connection of the PMOS transistor. In addition, due to the low power loss components being used in the switching element, the power consumption is low.

An amplifier may be used to drive the sound processor antenna. In particular, a class E amplifier or a class C amplifier may be used to drive the sound processor antenna. Both specified amplifier types have the advantage of being highly efficient. However, neither the switching element nor the inductive element lead to a limitation regarding the amplifier type used.

Within the first aspect, a method for switching a resonant frequency of a sound processor antenna in a sound processor unit of a cochlear implant system is disclosed, too. According to the method, the sound processor unit may comprise an electric circuit, which may comprise a sound processor antenna with a sound processor antenna capacitance and a sound processor antenna inductance. The sound processor antenna capacitance and the sound processor antenna inductance may be connected in series and form a resonant circuit.

The electric circuit of the sound processor unit may further comprise a switching element connected in series with the sound processor antenna capacitance and the sound processor antenna inductance. The electric circuit of the sound processor unit may further comprise an inductive element connected in parallel with the switching element.

The method may comprise:
  transitioning the switching element from a closed state to an open state such that the inductive element is caused to transition from a short-circuited state to a non-short-circuited state and the sound processor antenna is caused to transition from having a first resonant frequency to having a second resonant frequency which differs from the first resonant frequency; or
  transitioning the switching element from an open state to a closed state such that the inductive element is caused to transition from a non-short-circuited state to a short-circuited state and the sound processor antenna is caused to transition from having a second resonant frequency to having a first resonant frequency which differs from the second resonant frequency.

As already explained above in the context of the sound processor unit according the first aspect, by transitioning the switching element between the closed state and the open state, it is possible to switch the resonant frequency of the sound processor antenna between the first and the second resonance frequency. This allows the same type of sound processor unit to adapt to different resonant frequencies of an implant unit without having to exchange the sound processor antenna, for example. A user then no longer has to select a suitable sound processor antenna that matches their skin thickness from a set of sound processor antennas, such that user convenience is improved.

The transitioning of the switching element from the closed state to the open state or from the open state to the closed state may be caused or triggered by a processor, in particular a digital sound processor, of the electric circuit. The transitioning may be caused or triggered automatically by the processor. Thereby, user convenience can be improved further, since an action of the user is not necessary. The transitioning may also be caused or triggered by the processor in response to user input. This may give the user the possibility to influence the operation of the cochlear implant system according to their needs.

According to a second aspect, a sound processor unit of a cochlear implant system is disclosed. The sound processor unit may comprise a variable oscillator configured to generate an adjustable carrier frequency of an inductive link between the sound processor unit and an implant unit of the cochlear implant system.

The variable oscillator being configured to generate an adjustable carrier frequency of the inductive link is to be understood such that the variable oscillator is used for generating a carrier frequency of the inductive link, with a frequency adjustment of the variable oscillator leading to an adjustment of the carrier frequency. For example, the variable oscillator may generate an alternating voltage which may in addition be modulated by a signal voltage of a signal to be transmitted. The unmodulated or modulated alternating voltage may then be fed into a sound processor antenna of the sound processor unit, where it causes a corresponding electric current such that the sound processor antenna irradiates corresponding electromagnetic waves. Like this, if an inductive link between the sound processor antenna and an implant antenna of the implant unit is established, the alternating voltage generated by the variable oscillator acts as a carrier frequency of the inductive link. When the alternating voltage of the variable oscillator is adjusted, the carrier frequency is adjusted accordingly. In particular, the variable oscillator may be controlled, i.e. caused or triggered to adjust the generated alternating voltage, by a processor, in particular a digital sound processor, of an electric circuit of the sound processor unit. The variable oscillator may also be integrated into the processor.

The variable oscillator configured to generate an adjustable carrier frequency of the inductive link allows to adjust the carrier frequency in real time. This enables a quick and simple optimisation of the inductive link in case of varying mutual inductance such that both an improved power transmission and an improved communication between the sound processor unit and the implant unit can be provided. For example when the sound processor antenna is touched or moved, the mutual inductance is modified, and the adjustment of the carrier frequency allows a quick re-establishment of an optimal inductive link. In addition, the adjustment of the carrier frequency can be realised with low power consumption and has no impact on the modulation used for communicating with the implant unit. Furthermore, it allows the same type of sound processor unit to adapt to different types of implant units, which have different implant antennas with different resonant frequencies, without having to exchange the sound processor antenna. A user then no longer has to select a suitable sound processor antenna that matches their skin thickness from a set of sound processor antennas, such that user convenience is improved.

An amplifier may be used to drive the sound processor antenna. In particular, a class E, class C or class D amplifier may be used to drive the sound processor antenna. The variable oscillator configured to generate an adjustable carrier frequency of the inductive link does not lead to a limitation regarding the amplifier type used. The amplifier may be integrated into a processor, in particular a digital sound processor, of the sound processor unit.

Within the second aspect, a method for adjusting the carrier frequency of an inductive link between a sound processor unit and an implant unit of a cochlear implant system is disclosed, too. The method may comprise:
generating electromagnetic waves using a variable oscillator, wherein the frequency of the electromagnetic waves is varied over time between a lower limit frequency and an upper limit frequency;
measuring, as a function of the frequency of the electromagnetic waves, at least one parameter related to the cochlear implant system;
selecting a frequency based on the measurement;
using the selected frequency as a carrier frequency for the inductive link.

The variable oscillator used for generating the electromagnetic waves may be the same variable oscillator that is used for generating the adjustable carrier frequency of the inductive link as described above. Additionally or alternatively, the variable oscillator used for generating the electromagnetic waves may also be a different variable oscillator. In both cases, the generated alternating voltage of the variable oscillator is fed into a sound processor antenna of the sound processor unit in order to irradiate the electromagnetic waves. Varying the frequency of the electromagnetic waves over time between a lower limit frequency and an upper limit frequency may be performed by varying the frequency of the alternating voltage over time between a lower limit frequency and an upper limit frequency. The frequency of the electromagnetic waves may be varied continuously or stepwise over time. The lower and upper limit frequency may be selected based on properties of the sound processor antenna and/or an implant antenna of an implant unit, in particular based on a resonant frequency of the sound processor antenna and/or of the implant antenna. For example, the lower and upper limit frequency may form a frequency interval which includes the resonant frequency of the sound processor antenna and/or of the implant antenna. The lower and upper limit frequency may also be selected based on a previous or current carrier frequency of the inductive link. For example, the lower and upper limit frequency may form a frequency interval which includes the previous or current carrier frequency. Generating electromagnetic waves using a variable oscillator, wherein the frequency of the electromagnetic waves is varied over time between a lower limit frequency and an upper limit frequency, allows to cause a response of the cochlear implant system, on the basis of which the carrier frequency of the inductive link can then be adjusted.

Measuring, as a function of the frequency of the electromagnetic waves, at least one parameter related to the cochlear implant system is to be understood such that, by means of an appropriate sensor, any conceivable physical quantity that can be used to characterise the cochlear implant system is determined. This allows to determine, as a function of the frequency of the electromagnetic waves, a response of the cochlear implant system, on the basis of which the carrier frequency of the inductive link can then be adjusted.

Selecting a frequency based on the measurement is to be understood such that a frequency is selected for which the at least one measured parameter or any conceivable mathematical function of the at least one measured parameter attains a value that is advantageous in any conceivable way. For example, a frequency may be selected for which the at least one measured parameter attains a maximum and/or a minimum value. As another example, a frequency may be selected for which a sum, a difference, a product, a quotient, a derivative, an integral, or any other suitable mathematical function of the at least one measured parameter, or of more than one measured parameters, attains a maximum and/or a minimum value. As another example, a frequency may be selected for which the at least one measured parameter or any conceivable mathematical function of the at least one measured parameter exceeds or falls short of a predetermined threshold. Selecting a frequency based on the measurement allows to select a frequency, with which an optimised operation of the cochlear implant system, in particular of the inductive link, may be achieved.

Using the selected frequency as a carrier frequency for the inductive link may comprise adjusting the alternating voltage generated by the variable oscillator, so that the carrier frequency of the inductive link is adjusted accordingly. In particular, the variable oscillator may be controlled, i.e. caused or triggered to adjust the generated alternating voltage, by a processor of an electric circuit of the sound processor unit. The processor may be a digital sound processor, in particular. Using the selected frequency as a carrier frequency for the inductive link allows to operate the inductive link with an optimised carrier frequency.

The method according to the second aspect allows to identify and set a suitable carrier frequency for the inductive link in a quick and simple way. This enables optimised operation of the inductive link, for example with respect to power consumption or reliability of communication between the sound processor unit and the implant unit.

The method may be performed to identify and set an initial carrier frequency for the inductive link, for example after the cochlear implant system is switched on or after the inductive link has been established. Furthermore, the method may also be performed during operation of the cochlear implant system in order to adjust the carrier frequency of the inductive link such that an optimised operation can be achieved.

Generating the electromagnetic waves and measuring the at least one parameter may be performed simultaneously. This allows the method to be carried out particularly quick. In addition, this enables a simple way of determining the dependency of the at least one measured parameter on the frequency of the electromagnetic waves.

The at least one measured parameter may be the amplitude of a response signal from an implant antenna of the implant unit. In this case, the sound processor unit may send a trigger signal to which the implant units responds to by sending a response signal. This allows to adjust the carrier frequency such that the efficiency and reliability of the communication between the sound processor unit and the implant unit can be optimised.

Additionally, or alternatively, the at least one measured parameter may be a parameter related to a demodulated response signal from the implant antenna. In this case, a frequency may be selected and used as carrier frequency, for which the parameter related to the demodulated response signal fulfils a certain requirement, for example. The parameter may be, for example, a signal to noise ratio of the demodulated response signal, and the requirement may be, for example, that the signal to noise ratio exceeds a predetermined threshold or attains a maximum value. This allows to adjust the carrier frequency such that the reliability of the communication between the sound processor unit and the implant unit can be optimised.

Additionally, or alternatively, the at least one measured parameter may be the power consumption of the cochlear implant system. In this case, a frequency may be selected and used as carrier frequency, for which the measured power consumption attains a minimum value, for example. This allows to adjust the carrier frequency such that the power consumption of the cochlear implant system can be minimised.

At least one analog-digital-converter may be used for measuring the at least one parameter. Thereby, the measurement results can easily be processed and evaluated by the electric circuit of the sound processor unit, in particular by a processor of the electric circuit.

Additionally, or alternatively, at least one demodulator may be used for measuring the at least one parameter. For example in the case when the at least one measured parameter is a parameter related to a demodulated response signal from the implant antenna, a demodulator allows convenient measurement of the parameter.

The sound processor unit according to the second aspect may comprise means for performing the method according to the second aspect. More specifically, the sound processor unit may comprise:
  means for generating electromagnetic waves, wherein the frequency of the electromagnetic waves is variable;
  means for measuring at least one parameter related to the cochlear implant system;
  means for selecting a frequency;
  means for using the selected frequency as a carrier frequency for the inductive link.

This allows the sound processor unit according to the second aspect to perform a method according to the second aspect, and therefore to identify and set a suitable carrier frequency for the inductive link in a quick and simple way. Thereby, optimised operation of the inductive link, for example with respect to power consumption or reliability of communication between the sound processor unit and the implant unit, is enabled.

The means for generating electromagnetic waves may comprise at least one variable oscillator, at least one sound processor antenna, and/or at least one processor for controlling the at least one variable oscillator. The at least one processor may be at least one digital sound processor, in particular. The at least one variable oscillator may be integrated into the at least one processor. The means for measuring at least one parameter related to the cochlear implant system may comprise at least one measurement sensor and/or at least one analog-digital converter. The means for selecting a frequency may comprise at least one processor, in particular at least one digital sound processor. The means for using the selected frequency as a carrier frequency for the inductive link may comprise at least one variable oscillator and/or at least one processor for controlling the at least one variable oscillator. The at least one processor may be at least one digital sound processor, in particular. The at least one variable oscillator may be integrated into the at least one processor.

According to a third aspect, a method for determining at least one state and/or property related to a sound processor unit of a cochlear implant system is disclosed. The method may comprise:
  charging or at least attempting to charge a sound processor antenna of the sound processor unit and simultaneously measuring a charging voltage of the sound processor antenna;
  determining a rise time as the difference between an end time, at which the charging voltage exceeds a predetermined threshold, and a start time, at which the charging or charging attempt is started;
  determining at least one state and/or property related to the sound processor unit based on the determined rise time.

The term "rise time" is to be understood broadly and shall apply to either positive or negative step responses (a negative excursion may also be termed "fall time"). Accordingly, the description in present disclosure referring to a "rise time" shall always be understood to likewise pertain to a scenario of a "fall time", in which discharging voltage exceeds (i.e. falls short) of a predetermined threshold, even when not explicitly mentioned. Accordingly, the method according to the third aspect can also be implemented in that it comprises:

discharging or at least attempting to discharge a sound processor antenna of the sound processor unit and simultaneously measuring a discharging voltage of the sound processor antenna;

determining a fall time as the difference between an end time, at which the discharging voltage falls short of a predetermined threshold, and a start time, at which the discharging or discharging attempt is started;

determining at least one state and/or property related to the sound processor unit based on the determined fall time.

A person skilled in the art will readily understand that it does not make a difference for the present disclosure whether the sound processor antenna is charged and a rise time is determined, or whether the sound processor antenna is discharged and a fall time is determined. Therefore, the present disclosure only uses the terminology related to the first option, but it is always explicitly intended that this terminology is understood such that the second option is likewise covered. This does not only apply to the method according to the third aspect, but in particular also to the sound processor according to the third aspect, which will be explained further below. In addition, it also applies in particular to the appended claims.

Charging or at least attempting to charge a sound processor antenna of the cochlear implant system may comprise applying a direct voltage or temporally constant voltage to the sound processor antenna. Simultaneously measuring a charging voltage of the sound processor antenna may comprise measuring the charging voltage using a voltage sensor. Furthermore, measuring a charging voltage of the sound processor antenna may also comprise evaluating the measured charging voltage such that a charging voltage function is obtained. The charging voltage function may represent the charging voltage as a function of time. Charging or at least attempting to charge a sound processor antenna of the sound processor unit and simultaneously measuring a charging voltage of the sound processor antenna allows to provide the charging voltage as a function of time, for example represented by the charging voltage function.

Determining a rise time as the difference between an end time, at which the charging voltage exceeds a predetermined threshold, and a start time, at which the charging or charging attempt is started, may be performed simultaneously with the charging or charging attempt of the sound processor antenna. Furthermore, determining a rise time may be performed using a timer. For example, a timer may be started at the time, at which the charging or charging attempt is started, and stopped at the time, at which the charging voltage exceeds the predetermined threshold. Determining the rise time allows to provide a value of the rise time which can be evaluated such that at least one state and/or property related to the sound processor unit of the cochlear implant system may be determined.

Determining at least one state and/or property related to the sound processor unit of the cochlear implant system based on the determined rise time is to be understood such that any conceivable information that is indicative for a state of the sound processor unit and/or any conceivable physical quantity that can be used to characterise the sound processor unit may be determined. This allows to indicate a state and/or property related to the sound processor unit.

The method according to the third aspect in particular allows to obtain information about the state of operation of the sound processor unit of a cochlear implant system. This information can be used, for example, to optimise the operation. For example, a state and/or property of the sound processor unit can be determined, and the operation of the cochlear implant system can be optimised, for example with respect to power consumption or reliability of communication between the sound processor unit and the implant unit. Furthermore, the method according to the third aspect allows the information about the state of operation of the sound processor unit to be obtained particularly quickly, typically within a time interval of 100 µs, for example.

An amplifier may be used to charge or at least attempt to charge the sound processor antenna. In particular, a class D amplifier with a general purpose input and output may be used to charge or at least attempt to charge the sound processor antenna. Using a class D amplifier has the advantage that the MOS transistors of the class D amplifier can be used as the general purpose input and output. The amplifier may be integrated into a processor, in particular a digital sound processor of the sound processor unit.

Generally, a full chipset which may provide any of the functionality described herein. The Chipset may be provided which may contain one or more of a class D amplifier, a timer, a DSP, memories, a GPIO. It may also be possible to disconnect the class D amplifier and use standard GPIO instead thereof.

Determining at least one state and/or property related to the sound processor unit may comprise:

determining that a sound processor antenna is connected to the sound processor unit, and determining at least one property related to the sound processor antenna based on the determined rise time; or determining that no sound processor antenna is connected to the sound processor unit. Determining whether or not a sound processor antenna is connected to the sound processor unit allows to optimise the operation of the cochlear implant system accordingly. For example, the system or components of the system may be deactivated or put into a stand-by mode if it is determined that no sound processor antenna is connected to the sound processor unit, or the system or components of the system may be activated or re-activated or put into a mode of normal operation if it is determined that a sound processor antenna is connected to the sound processor unit. Determining at least one property related to the sound processor antenna based on the determined rise time is to be understood such that any conceivable physical quantity that can be used to characterise the sound processor antenna may be determined. This allows to indicate a property related to the sound processor antenna.

Determining at least one property related to the sound processor antenna based on the determined rise time may comprise determining a resonant frequency of the sound processor antenna based on the determined rise time. For example, the resonant frequency of the sound processor antenna may be determined by comparing the determined rise time with rise times stored in a database, which associates different rise times with different resonant frequencies. Determining a resonant frequency of the sound processor antenna based on the determined rise time allows to identify the resonant frequency of the sound processor antenna which is connected to the sound processor unit. For example, the cochlear implant system can be configured accordingly in order to adapt to the resonant frequency of the sound processor antenna.

Additionally or alternatively, determining at least one property related to the sound processor antenna based on the determined rise time may comprise determining an antenna type of the sound processor antenna based on the determined rise time. For example, the antenna type of the sound processor antenna may be determined by comparing the determined rise time with rise times stored in a database, which associates different rise times with different antenna types. Determining an antenna type of the sound processor antenna allows to identify the antenna type of the sound processor antenna which is connected to the sound processor unit. For example, the cochlear implant system can be configured accordingly in order to adapt to the type of the sound processor antenna.

The method according to the third aspect may be performed during a booting process of the sound processor unit. This allows to determine whether or not a sound processor antenna is connected to the sound processor unit, and to determine at least one property related to the sound processor antenna, right after the sound processor unit is switched on and starts its operation.

Additionally or alternatively, the method according to the third aspect may be performed after initiation by manual user input. For example, the user may perform and/or indicate an establishment or re-establishment of a connection between the sound processor unit and a sound processor antenna. Therefore, performing the method according to the third aspect after initiation by manual user input allows to determine whether or not a sound processor antenna is really connected to the sound processor unit, and to determine at least one property related to the sound processor antenna in case of an establishment or re-establishment of a connection to the sound processor unit.

In the case where determining at least one property related to the sound processor antenna based on the determined rise time comprises determining a resonant frequency of the sound processor antenna based on the determined rise time and/or determining an antenna type of the sound processor antenna based on the determined rise time, the method according to the third aspect may further comprise at least one of the following:

determining a resonant frequency of the sound processor antenna based on the determined antenna type;

using the resonant frequency of the sound processor antenna, which has been determined based on the determined rise time and/or based on the determined antenna type, as a carrier frequency for an inductive link between the sound processor unit and an implant unit of the cochlear implant system;

performing a method according to the second aspect, wherein the lower limit frequency and the upper limit frequency are selected based on the determined resonant frequency of the sound processor antenna.

If an antenna type of the sound processor antenna has been determined based on the determined rise time, determining a resonant frequency of the sound processor antenna based on the determined antenna type may be performed. For example, the resonant frequency may be determined by comparing the determined antenna type with antenna types stored in a database, which associates different antenna types with different resonant frequencies. This allows a determination of a resonant frequency of the sound processor antenna via the antenna type, for example also in cases where the resonant frequency has not initially been determined based on the determined rise time. However, determining a resonant frequency of the sound processor antenna based on the determined antenna type may be omitted, if a resonant frequency of the sound processor antenna has already been determined based on the determined rise time. This increases the efficiency of the method, since the number of actions to be performed is reduced.

The resonant frequency of the sound processor antenna, which has been determined based on the determined rise time and/or based on the determined antenna type, may then be used as a carrier frequency for an inductive link between the sound processor unit and an implant unit of the cochlear implant system. This allows to establish the inductive link with a suitable carrier frequency.

Additionally or alternatively, the carrier frequency of the inductive link between the sound processor unit and the implant unit may be adjusted by performing a method according to the second aspect. In this case, the lower and upper limit frequency for the method according to the second aspect may be selected, for example, such that the lower and upper limit frequency form a frequency interval which includes the determined resonant frequency of the sound processor antenna. Thereby, optimised operation of the inductive link, for example with respect to power consumption or reliability of communication between the sound processor unit and the implant unit, is achieved.

Overall, the operation of the cochlear implant system can be optimised, in particular because the information about the state of operation of the sound processor unit, which is obtained from the rise time, is used as a basis for optimising the operation of the cochlear implant system by means of performing a method according to the second aspect, for example.

Within the third aspect, a sound processor unit of a cochlear implant system is disclosed, too. The sound processor unit according to the third aspect may comprise means for performing the method according to the third aspect. More specifically, the sound processor unit may comprise:

means for charging or at least attempting to charge a sound processor antenna of the sound processor unit and means for simultaneously measuring a charging voltage of the sound processor antenna;

means for determining a rise time as the difference between an end time, at which the charging voltage exceeds a predetermined threshold, and a start time, at which the charging or charging attempt is started;

means for determining at least one state and/or property related to the sound processor unit based on the determined rise time.

This allows the sound processor unit according to the third aspect to perform a method according to the third aspect, and therefore to obtain information about the state of operation of the sound processor unit. This information can be used, for example, to optimise the operation.

The means for charging or at least attempt to charge a sound processor antenna, means for simultaneously measuring a charging voltage, means for determining a rise time, and means for determining at least one state and/or property related to the sound processor unit may comprise at least one processor, in particular at least one digital sound processor of a sound processor unit, and/or at least one amplifier, in particular at least one class D amplifier with a general purpose input and output. The at least one amplifier, in particular the at least one class D amplifier with general input and output may be integrated into the at least one processor, in particular the at least one digital sound processor. Using a class D amplifier has the advantage that the MOS transistors of the class D amplifier can be used as the general purpose input and output.

For the sound processor unit according to the third aspect, the means for determining at least one state and/or property related to the sound processor unit based on the determined rise time may comprise means for determining a resonant frequency of a sound processor antenna of the sound processor unit based on the determined rise time and/or means for determining an antenna type of a sound processor antenna of the sound processor unit based on the determined rise time. In this case, the sound processor unit may further comprise at least one of the following:

means for determining a resonant frequency of the sound processor antenna based on the determined antenna type;

means for using the resonant frequency of the sound processor antenna, which has been determined based on the determined rise time and/or based on the determined antenna type, as a carrier frequency for an inductive link between the sound processor unit and an implant unit of the cochlear implant system;

means for performing a method according to the second aspect.

This allows, as already explained above, to establish the inductive link with a suitable carrier frequency, and/or to adjust the carrier frequency of the inductive link such that optimised operation of the inductive link, for example with respect to power consumption or reliability of communication between the sound processor unit and the implant unit, can be achieved.

The means for determining a resonant frequency of the sound processor antenna based on the determined antenna type may comprise at least one processor, in particular at least one digital sound processor, and/or at least one amplifier, in particular at least one class D amplifier with a general purpose input and output. The at least one amplifier may be integrated into the at least one processor. The means for using the resonant frequency of the sound processor antenna as a carrier frequency for an inductive link between the sound processor unit and an implant unit of the cochlear implant system may comprise at least one variable oscillator, at least one processor for controlling the at least one variable oscillator, and/or at least one amplifier. In particular, the at least one processor for controlling the at least one variable oscillator may be at least one digital sound processor. In particular, the at least one amplifier may be at least one class D amplifier with a general purpose input and output. Using a class D amplifier has the advantage that the MOS transistors of the class D amplifier can be used as the general purpose input and output. The at least one variable oscillator and/or the at least one amplifier may be integrated into the at least one processor.

Within any of the first, second and third aspects, a cochlear implant system is disclosed, too. The cochlear implant system may comprise a sound processor unit according to the first aspect. Alternatively, the cochlear implant system may comprise a sound processor unit according to the second aspect. Alternatively, the cochlear implant system may comprise a sound processor unit according to the third aspect. Alternatively, the cochlear implant system may comprise a sound processor unit according to a combination of the first, second and third aspects. Additionally, the cochlear implant system may comprise an implant unit. By using a sound processor unit according to any of the first, second and third aspects, in particular a sound processor unit according to all three aspects, in combination with an implant unit, a cochlear implant system that is improved as described above can be provided.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

Figure 1:
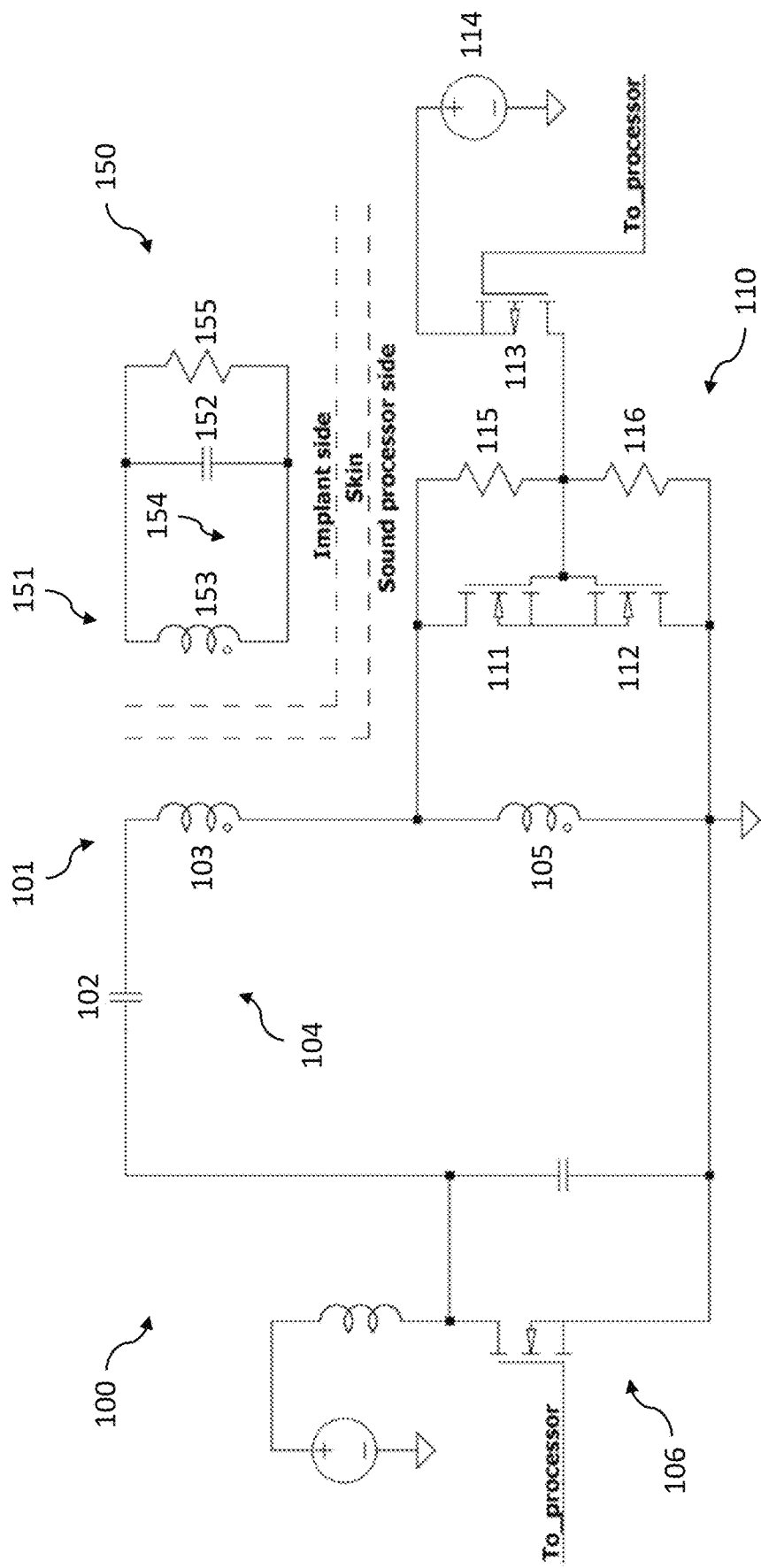
FIG. 1 shows a schematic circuit diagram of an electric circuit of a sound processor unit including a switching element according to the first aspect and a schematic circuit diagram of an electric circuit of an implant unit.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include micro-electronic-mechanical systems (MEMS), integrated circuits (e.g. application specific), microprocessors, microcontrollers, digital signal processors (DSPs), field programmable gate arrays (FPGAs), programmable logic devices (PLDs), gated logic, discrete hardware circuits, printed circuit boards (PCB) (e.g.

flexible PCBs), and other suitable hardware configured to perform the various functionality described throughout this disclosure, e.g. sensors, e.g. for sensing and/or registering physical properties of the environment, the device, the user, etc. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing device (or hearing instrument, hearing assistance device) may be or include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. 'Improving or augmenting the hearing capability of a user' may include compensating for an individual user's specific hearing loss. The "hearing device" may further refer to a device such as a hearable, an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of the middle ear of the user or electric signals transferred directly or indirectly to the cochlear nerve and/or to the auditory cortex of the user.

A "hearing system" refers to a system comprising one or two hearing devices, and a "binaural hearing system" or a bimodal hearing system refers to a system comprising two hearing devices where the devices are adapted to cooperatively provide audible signals to both of the user's ears either by acoustic stimulation only, acoustic and mechanical stimulation, mechanical stimulation only, acoustic and electrical stimulation, mechanical and electrical stimulation or only electrical stimulation. The hearing system, the binaural hearing system or the bimodal hearing system may further include one or more auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of a remote control, a remote microphone, an audio gateway device, a wireless communication device, e.g. a mobile phone (such as a smartphone) or a tablet or another device, e.g. comprising a graphical interface, a public-address system, a car audio system or a music player, or a combination thereof. The audio gateway may be adapted to receive a multitude of audio signals such as from an entertainment device like a TV or a music player, a telephone apparatus like a mobile telephone or a computer, e.g. a PC. The auxiliary device may further be adapted to (e.g. allow a user to) select and/or combine an appropriate one of the received audio signals (or combination of signals) for transmission to the at least one hearing device. The remote control is adapted to control functionality and/or operation of the at least one hearing device. The function of the remote control may be implemented in a smartphone or other (e.g. portable) electronic device, the smartphone/electronic device possibly running an application (APP) that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to (relatively) enhance a target acoustic source among a multitude of acoustic sources in the user's environment and/or to attenuate other sources (e.g. noise). In one aspect, the directional system is adapted to detect (such as adaptively detect) from which direction a particular part of the microphone signal originates. This may be achieved by using conventionally known methods. The signal processing unit may include an amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal to the ear of the user, a mechanical stimulation applied transcutaneously or percutaneously to the skull bone, an electrical stimulation applied to auditory nerve fibers of a cochlea of the user. In some hearing devices, the output unit may include one or more output electrodes for providing the electrical stimulations such as in a cochlear implant, or the output unit may include one or more vibrators for providing the mechanical stimulation to the skull bone.

A cochlear implant system typically includes i) an external part for picking up and processing sound from the environment, and for determining sequences of pulses for stimulation of the electrodes in dependence on the sound from the environment, ii) a (typically wireless, e.g. inductive) transcutaneous communication link for transmitting information about the stimulation sequences and/or for transferring energy to iii) an implanted part allowing the stimulation to be generated and applied to a number of electrodes, which are implantable in different locations of the cochlea allowing a stimulation of different frequencies of the audible range. Such systems are e.g. described in U.S. Pat. No. 4,207,441 and in U.S. Pat. No. 4,532,930.

In an aspect, the hearing device comprises multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea.

Now referring to FIG. 1, a schematic circuit diagram of an electric circuit of a sound processor unit according to the first aspect and a schematic circuit diagram of an electric circuit of an implant unit is shown. The electric circuit (100) of the sound processor unit comprises a sound processor antenna (101) with a sound processor antenna capacitance (102) and a sound processor antenna inductance (103). The sound processor antenna capacitance (102) and the sound processor antenna inductance (103) are connected in series and form a resonant circuit (104).

As shown in FIG. 1, the sound processor antenna (101) of the sound processor unit with the sound processor antenna capacitance (102) and the sound processor antenna inductance (103) allows the sound processor unit to transmit and/or receive signals to and/or from an implant unit which is inductively linked to the sound processor unit, as well as to transfer electric power to the inductively linked implant unit. In FIG. 1, a schematic circuit diagram of an electric circuit (150) of an implant unit is shown, too. The electric circuit (150) of the implant unit comprises an implant antenna (151) with an implant antenna capacitance (152) and an implant antenna inductance (153). The implant antenna capacitance (152) and the implant antenna inductance (153) are likewise connected in series and form a resonant circuit (154). Furthermore, the electric circuit (150) of the implant unit comprises an electric load, which is schematically represented by the resistance (155). As shown in FIG. 1, the inductive link between the sound processor unit and the implant unit is established transcutaneously, i.e. penetrating the skin of the user.

The electric circuit (100) of the sound processor unit further comprises a switching element (110) connected in series with the sound processor antenna capacitance (102) and the sound processor antenna inductance (103). The electric circuit (100) of the sound processor unit further comprises an inductive element (105) connected in parallel with the switching element (110). As FIG. 1 shows, when the switching element (110) is in a closed state, electric current flow over the switching element (110) is enabled, and therefore the inductive element (105) is in a short-circuited state. The resonant circuit (104) of the sound processor antenna (101) is then formed by the sound processor antenna capacitance (102) and the sound processor antenna inductance (104). In this configuration, the sound processor antenna (101) has a first resonant frequency, which is not influenced by the inductive element (105). As FIG. 1 shows further, when the switching element (110) is in an open state, electric current flow over the switching element (110) is interrupted, and therefore the inductive element (105) is in a non-short-circuited state. The resonant circuit (104) of the sound processor antenna (101) is then formed by the sound processor antenna capacitance (102), the sound processor antenna inductance (103) and the inductive element (105). In this configuration, the sound processor antenna (101) has a second resonant frequency, which is influenced by the inductive element (105) and therefore differs from the first resonant frequency.

By transitioning the switching element (110) between the closed state and the open state, it is possible to switch the resonant frequency of the sound processor antenna (101) between the first and the second resonance frequency. This allows the sound processor unit to adapt to different resonant frequencies of the implant unit, which correspond to different skin thicknesses of a user, without having to exchange the sound processor antenna (101). The user then no longer has to select a suitable sound processor antenna that matches their skin thickness from a set of sound processor antennas, such that user convenience is improved.

The switching element (110) shown in FIG. 1 comprises two transistors (111, 112) for short circuiting the inductive element (105). Thereby, a cost-effective, yet reliable switching element (110) can be provided without numerous electronic components being required. However, a minimum of two transistors (111, 112) are needed as the current flowing through the transistors (111, 112) is sinusoidal and flows in both directions (quadratic behaviour). Furthermore, the switching element (110) comprises a third transistor (113) for controlling the two transistors (111, 112) that are used to short circuit the inductive element (105). Thereby, it is possible to simultaneously control the at least two transistors (111, 112) that can short circuit the inductive element (105). The transistors (111, 112, 113) of the switching element (110) are MOS transistors, which meet the high space requirements of cochlear implant systems and are advantageous in that they are easy to control due to their saturation state and in that they have a low power loss.

More specifically, the switching element (110) shown in FIG. 1 comprises a first NMOS transistor (111) and a second NMOS transistor (112) for short circuiting the inductive element (105), as well as a PMOS transistor (113) for controlling the two NMOS transistors (111, 112). Furthermore, the switching element (110) comprises a DC voltage supply (114), a first resistor (115) and a second resistor (116). The DC voltage supply (114) comprises a positive terminal and a negative terminal. The first and second NMOS transistor (111, 112) and the PMOS transistor (113) comprise in each case a gate connection, a source connection and a drain connection. The first and second resistor (115, 116) comprise in each case a first end connection and a second end connection. The negative terminal of the DC voltage supply (114) is electrically conductively connected to ground. The positive terminal of the DC voltage supply (114) is electrically conductively connected to the source connection of the PMOS transistor (113). The drain connection of the PMOS transistor (113) is electrically conductively connected to the first end connection of the first resistor (115), to the first end connection of the second resistor (116), to the gate connection of the first NMOS transistor (111), and to the gate connection of the second NMOS transistor (112). The source connection of the first NMOS transistor (111) is electrically conductively connected to the source connection of the second NMOS transistor (112). The second end connection of the first resistor (115) is electrically conductively connected to the drain connection of the first NMOS transistor (111). The second end connection of the second resistor (116) is electrically conductively connected to the drain connection of the second NMOS transistor (112). The switching element (110) comprising a DC voltage supply (114), a first NMOS transistor (111), a second NMOS transistor (112), a PMOS transistor (113), a first resistor (115) and a second resistor (116), which are electrically conductively connected to one another and to ground as explained above, is a particularly advantageous realization with respect to the adaptation to a sinusoidal wave form of the current, with respect to easy control from a digital sound processor of the sound processor unit, and with respect to low power consumption.

The transitioning of the switching element (105) from the closed state to the open state or from the open state to the closed state is caused or triggered here by a digital sound processor of the electric circuit (100). As FIG. 1 shows, the digital sound processor is electrically conductively connected to the gate connection of the PMOS transistor (113). Here, the transitioning is caused or triggered by the processor in response to user input, which gives the user the possibility to influence the operation of the cochlear implant system according to their needs. However, an automatic causing or triggering the transitioning by the digital sound processor is likewise conceivable.

As shown in FIG. 1, a class E amplifier (106) is used to drive the sound processor antenna (101). The class E amplifier (106) has the advantage of being highly efficient. However, neither the switching element nor the inductive element lead to a limitation regarding the amplifier type used and therefore, other amplifier types are also conceivable.

Figure 2:
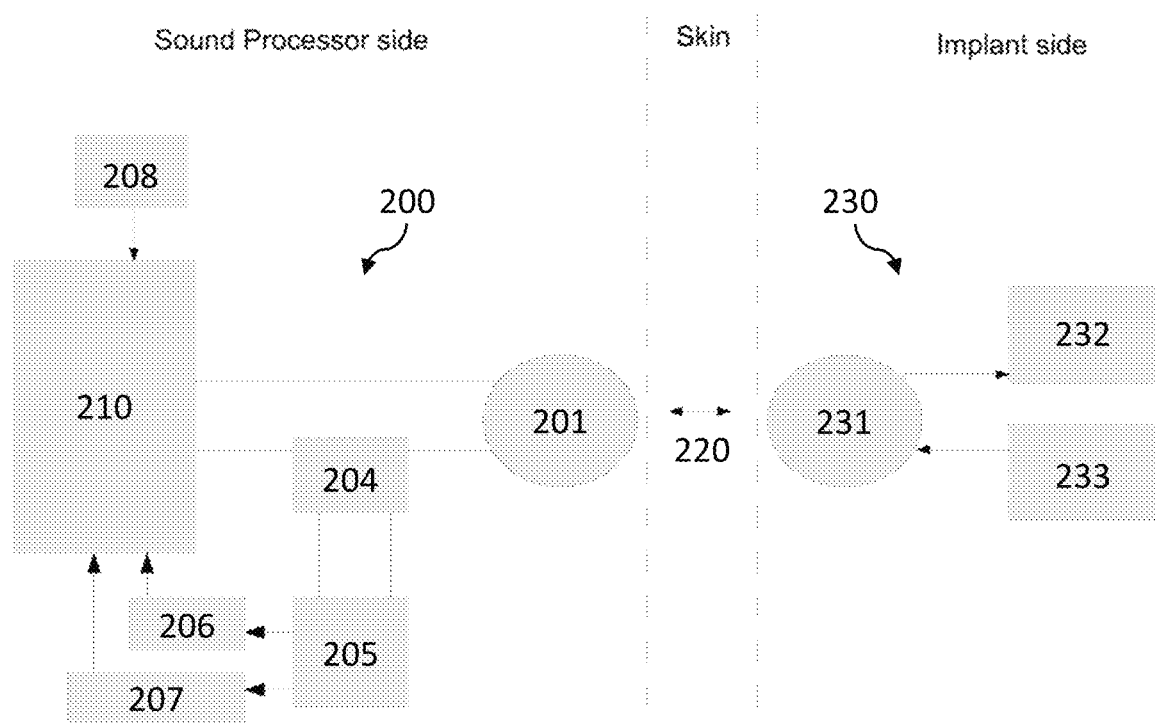
FIG. 2 shows a schematic circuit diagram of an electric circuit of a sound processor unit according to the second and third aspect and a schematic circuit diagram of an electric circuit of an implant unit.

FIG. 2 shows a schematic circuit diagram of an electric circuit of a sound processor unit according to the second and third aspect and a schematic circuit diagram of an electric circuit of an implant unit. With respect to the second aspect, the electric circuit (200) of the sound processor unit comprises a variable oscillator configured to generate an adjustable carrier frequency of an inductive link (220) between the sound processor unit and the implant unit. In FIG. 2, the variable oscillator is integrated into a digital sound processor (210) of the sound processor unit, and a voltage source (208) is used to supply electric power to the digital sound processor (210) including the variable oscillator. The electric circuit (230) of the implant unit is shown only schematically and comprises an implant antenna (231) as well as an electric load (232) and a modulator (233).

The variable oscillator integrated into the digital sound processor (210) is used for generating a carrier frequency of the inductive link (220), with a frequency adjustment of the variable oscillator leading to an adjustment of the carrier frequency. In more detail, the variable oscillator generates an alternating voltage which is in addition modulated by a signal voltage of a signal to be transmitted. However, the modulation is not mandatory, and an unmodulated alternating voltage is also conceivable. In the embodiment of FIG. 2, the modulated alternating voltage is fed into the sound processor antenna (201) of the sound processor unit, where it causes a corresponding electric current such that the sound processor antenna (201) irradiates corresponding electromagnetic waves. Like this, the alternating voltage generated by the variable oscillator acts as a carrier frequency of the inductive link (220) between the sound processor antenna (201) and the implant antenna (231). When the alternating voltage of the variable oscillator is adjusted, the carrier frequency is adjusted accordingly. Here, the variable oscillator is controlled, i.e. caused or triggered to adjust the generated alternating voltage, by the digital sound processor (210) of the sound processor unit, into which it is integrated.

With the variable oscillator being configured to generate an adjustable carrier frequency of the inductive link (220), it is possible to adjust the carrier frequency in real time. This enables a quick and simple optimisation of the inductive link (220) in case of varying mutual inductance such that both an improved power transmission and an improved communication between the sound processor unit and the implant unit can be provided. In addition, the adjustment of the carrier frequency can be realised with low power consumption and has no impact on the modulation used for communicating with the implant unit. Furthermore, it allows the same type of sound processor unit to adapt to different types of implant units, which have different implant antennas with different resonant frequencies, without having to exchange the sound processor antenna (201). A user then no longer has to select a suitable sound processor antenna that matches their skin thickness from a set of sound processor antennas, such that user convenience is improved.

Furthermore, as shown in FIG. 2, an amplifier is used to drive the sound processor antenna (201). Here, a class D amplifier is used, which is likewise integrated into the digital sound processor (210). However, the variable oscillator configured to generate an adjustable carrier frequency of the inductive link (220) does not lead to a limitation regarding the amplifier type used and therefore, other amplifier types are also conceivable.

Figure 3:
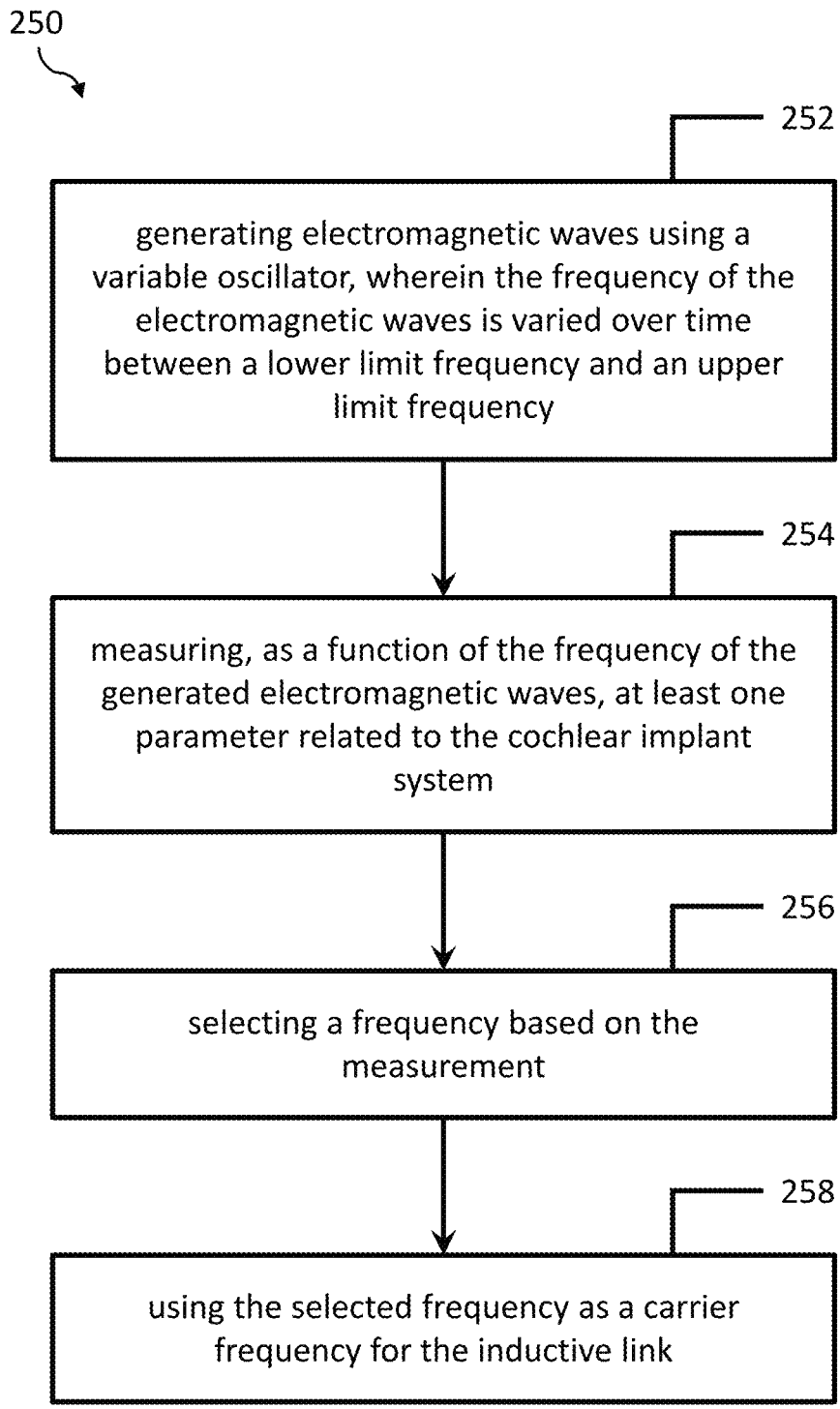
FIG. 3 shows a schematic flow diagram illustrating operations performed in accordance with an exemplary embodiment of a method according to the second aspect.

FIG. 3 shows a schematic flow diagram illustrating operations performed in accordance with an exemplary embodiment of a method according to the second aspect. According to this embodiment, the method (250) for adjusting the carrier frequency of an inductive link between a sound processor unit and an implant unit of a cochlear implant system comprises:

generating (252) electromagnetic waves using a variable oscillator, wherein the frequency of the electromagnetic waves is varied over time between a lower limit frequency and an upper limit frequency;

measuring (254), as a function of the frequency of the electromagnetic waves, at least one parameter related to the cochlear implant system;

selecting (256) a frequency based on the measurement;

using (258) the selected frequency as a carrier frequency for the inductive link.

Although the different elements are arranged in a particular order in the flow diagram of FIG. 3, any reasonable way of performing the method, which is known to a person skilled in the art, and which may likewise result in a different order or no order at all, i.e. the different elements being for example performed simultaneously, is conceivable. In particular, generating (252) electromagnetic waves and measuring (254) at least one parameter are performed simultaneously in the embodiment of the method of FIG. 3.

The embodiment of the method of FIG. 3 allows to identify and set a suitable carrier frequency for the inductive link in a quick and simple way. This enables optimised operation of the inductive link, for example with respect to power consumption or reliability of communication between the sound processor unit and the implant unit.

The sound processor unit according to the second and third aspect, which has been explained above in the context of FIG. 2, is configured to perform a method according to the second aspect, in particular the embodiment of the method of FIG. 3. For this purpose, the sound processor unit comprises means (201, 210) for generating electromagnetic waves, wherein the frequency of the electromagnetic waves is variable. These means for generating electromagnetic waves involve the variable oscillator integrated into the digital sound processor (210), the sound processor antenna (201), as well as the digital sound processor (210) that controls the variable oscillator. The sound processor unit further comprises means (204, 205, 206, 207) for measuring at least one parameter related to the cochlear implant system. These means for measuring involve a coupled inductance (204), a rectifier (205), an analog-digital-converter (206) and a demodulator (207). The sound processor unit further comprises means (210) for selecting a frequency, which is in this case the digital sound processor (210). The sound processor unit further comprises means (210) for using the selected frequency as a carrier frequency for the inductive link (220), which involve the variable oscillator integrated into the digital sound processor (210) and the digital sound processor (210) that controls the variable oscillator.

In the particular embodiment of the method of FIG. 3, when this method is performed by the sound processor unit of FIG. 2, the variable oscillator used for generating (252) the electromagnetic waves is the variable oscillator which is integrated into the digital sound processor (210), and which is used for generating the adjustable carrier frequency of the inductive link (220). However, it is also conceivable that the variable oscillator used for generating (252) the electromagnetic waves is a different variable oscillator, the generated alternating voltage of which is likewise fed into the sound processor antenna (201). Furthermore, in the embodiment of the method of FIG. 3, the at least one measured parameter is the amplitude of a response signal from the implant antenna (231). For measuring this amplitude, the analog-digital-converter (206) is used in conjunction with the coupled inductance (204) and the rectifier (205). However, the coupled inductance (204) and the rectifier (205) may be omitted if other parameters are measured as the at least one parameter related to the cochlear implant system. Measuring the amplitude of a response signal from the implant antenna allows to adjust the carrier frequency such that the efficiency and reliability of the communication between the sound processor unit and the implant unit is optimised, and by using the analog-digital converter (206), the measurement results can easily be processed and evaluated by the digital sound processor (210) of the electric circuit. However, it is also conceivable that the at least one measured parameter is a parameter related to a demodulated response signal from the implant antenna. Regarding this, the means for measuring of the electric circuit (200) of the sound processor unit also involve a demodulator (207), which is used to measure the parameter related to a demodulated response signal from the implant antenna. In addition, the electric circuit (230) of the implant unit also comprises a modulator (233) to generate a modulated response signal. Measuring a parameter related to a demodulated response signal from the implant antenna also allows to adjust the carrier frequency such that the efficiency and reliability of the communication between the sound processor unit and the implant unit is optimised. Furthermore, it is also conceivable that the at least one measured parameter is the power consumption of the cochlear implant system. This allows to adjust the carrier frequency such that the power consumption of the cochlear implant system is minimised.

Figure 4:
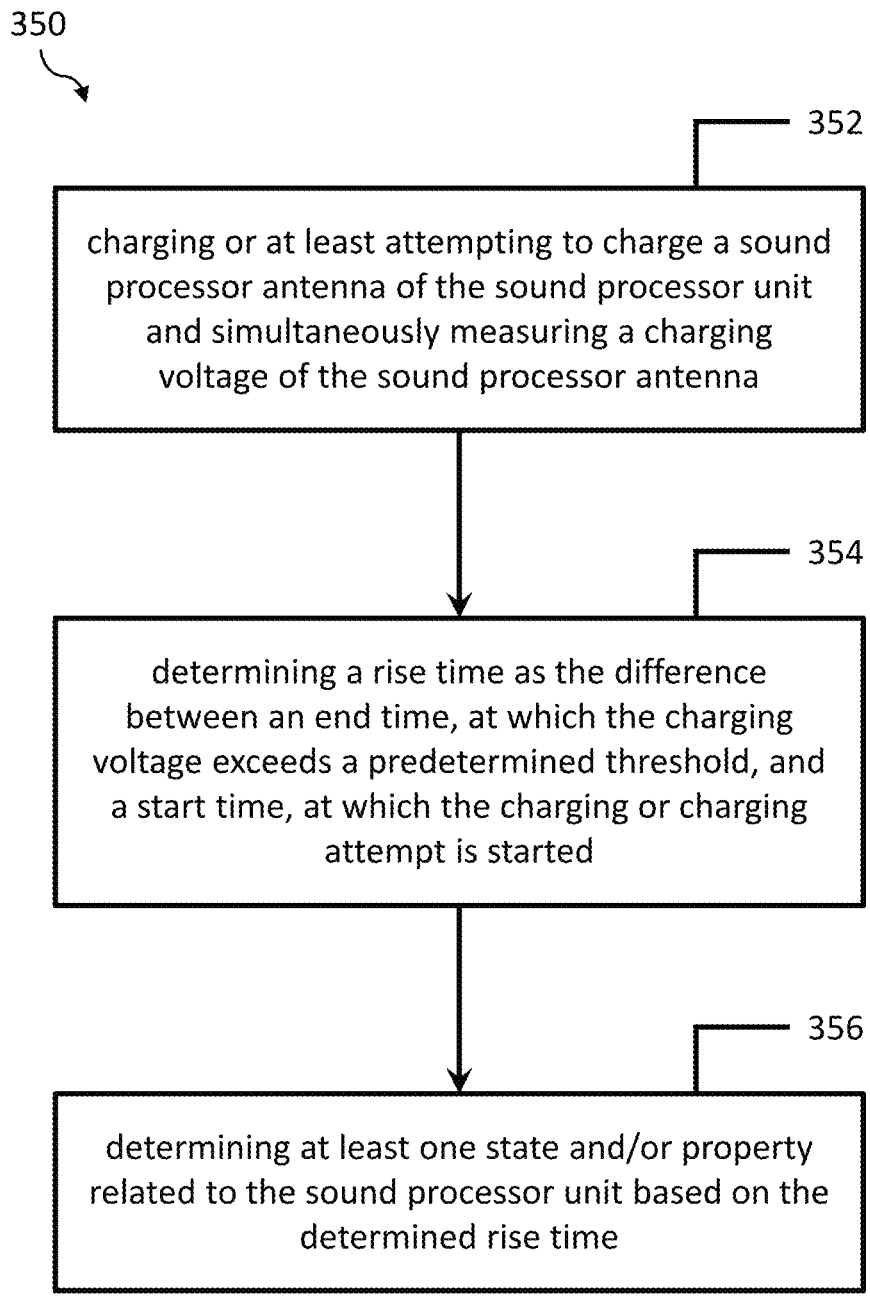
FIG. 4 shows a schematic flow diagram illustrating operations performed in accordance with an exemplary embodiment of a method according to the third aspect.

FIG. 4 shows a schematic flow diagram illustrating operations performed in accordance with an exemplary embodiment of a method according to the third aspect. According to this embodiment, the method (350) for determining at least one state and/or property related to a sound processor unit of a cochlear implant system comprises:

charging (352) or at least attempting to charge a sound processor antenna of the sound processor unit and simultaneously measuring a charging voltage of the sound processor antenna;

determining (354) a rise time as the difference between an end time, at which the charging voltage exceeds a predetermined threshold, and a start time, at which the charging or charging attempt is started;

determining (356) at least one state and/or property related to the sound processor unit based on the determined rise time.

Although the different elements are arranged in a particular order in the flow diagram of FIG. 4, any reasonable way of performing the method, which is known to a person skilled in the art, and which may likewise result in a different order or no order at all, i.e. the different elements being for example performed simultaneously, is conceivable.

The embodiment of the method of FIG. 4 allows to obtain information about the state of operation of the sound processor unit of a cochlear implant system. This information can be used to optimise the operation. Furthermore, the embodiment of the method of FIG. 4 allows the information to be obtained particularly quickly.

Figure 5:
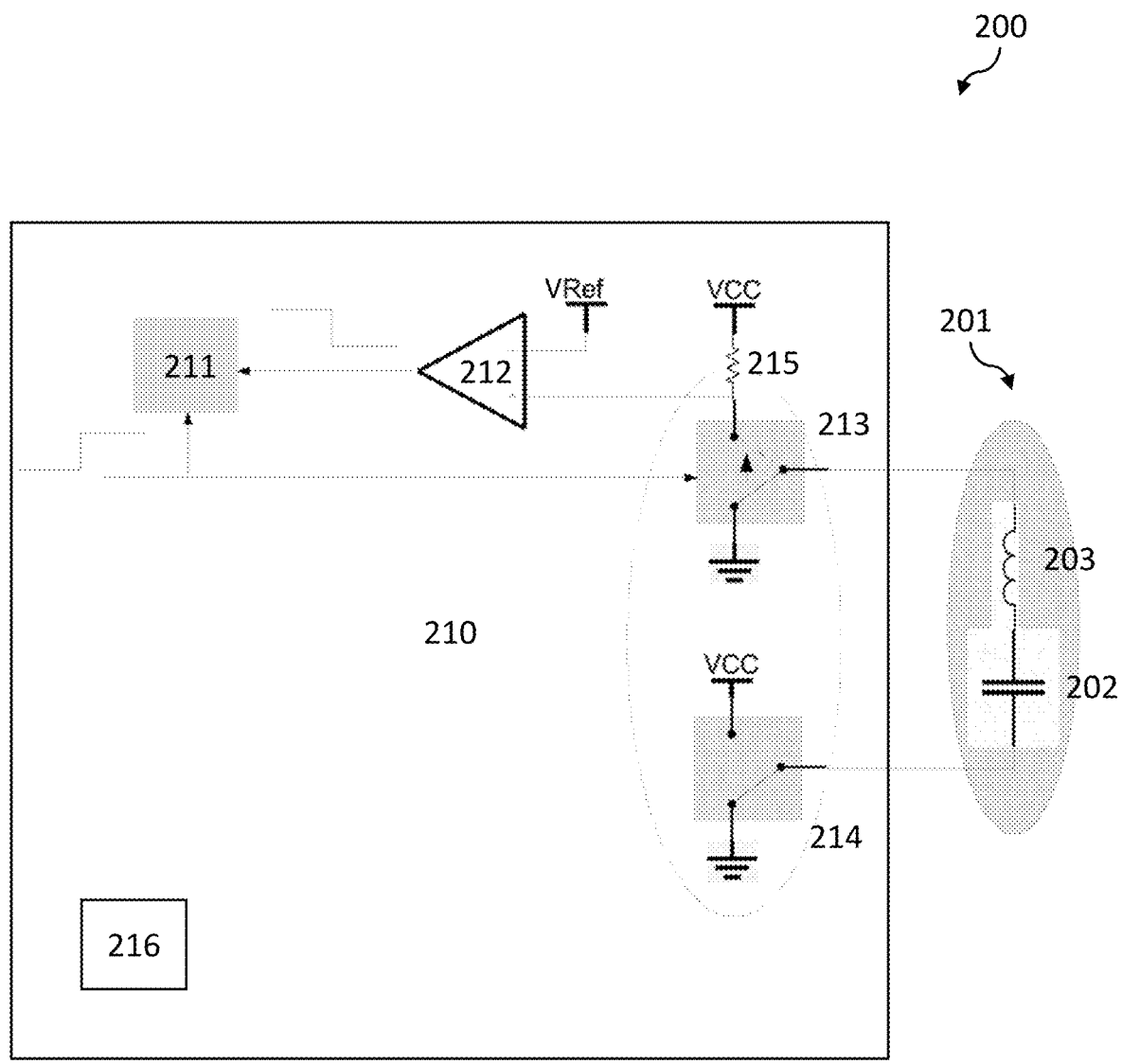
FIG. 5 shows a schematic circuit diagram of an electric circuit of a sound processor unit according to the third aspect.

FIG. 5 shows a schematic circuit diagram of an electric circuit of a sound processor unit according to the third aspect. More specifically, FIG. 5 shows a detailed view of the schematic circuit diagram of FIG. 2, where only elements that are primarily relevant for the third aspect are shown in more detail and elements that are not primarily relevant for the third aspect are omitted. Nevertheless, a sound processor unit with an electric circuit comprising only the elements shown in FIG. 5 would function as a stand-alone sound processor unit according to the third aspect. With the electric circuit (200) shown in FIG. 5, the sound processor unit is configured to perform a method according to the third aspect, in particular the embodiment shown in FIG. 4, and comprises means for performing such a method. More specifically, the electric circuit (200) comprises a digital sound processor (210), into which a class D amplifier with a general purpose input and output is integrated. As will be explained below, the digital sound processor (210) acts as:

means for charging or at least attempting to charge a sound processor antenna (201) of the sound processor unit and means for simultaneously measuring a charging voltage of the sound processor antenna (201);

means for determining a rise time as the difference between an end time, at which the charging voltage exceeds a predetermined threshold, and a start time, at which the charging or charging attempt is started;

means for determining at least one state and/or property related to the sound processor unit based on the determined rise time.

As shown in FIG. 5, the digital sound processor (210) is electrically conductively connected to a voltage source, which supplies a charging control voltage (VCC). The digital sound processor (210) further comprises a first switch (213) and a second switch (214), which are both realised using MOS transistors and indicated only schematically in FIG. 5. The digital sound processor (210) supplies the charging control voltage (VCC) to a first connection of the first and second switch (213, 214) in each case, with an intermediate pullup resistor (215) being additionally integrated between the charging control voltage supply and the first connection in case of the first switch (213). In addition, the first and second switch (213, 214) both comprise a second connection, which is electrically conductively connected to ground in each case. Furthermore, the first and second switch (213, 214) of the digital sound processor (210) comprise in each case a third connection, which is electrically conductively connected in each case to the sound processor antenna (201) having a sound processor antenna capacitance (202) and a sound processor antenna inductance (203). The digital sound processor (210) further comprises a timer (211) and a comparator (212). Moreover, a class D amplifier (not shown in FIG. 5) with a general purpose input and output is used to charge or at least attempt to charge the sound processor antenna (201), the class D amplifier being integrated into the sound processor unit (210), as explained above in the context of FIG. 2. Using a class D amplifier has the advantage that the MOS transistors of the class D amplifier can be used as the general purpose input and output.

To perform the method shown in FIG. 4, both switches (213, 214) are initially applied to ground and thus, the antenna (201) is completely discharged. After a waiting time of 100 µs at maximum, both switches (213, 214) are applied to the respective first connection that is connected, directly or via the pullup resistor (215), to the charging control voltage (VCC), and therefore, the antenna starts to be charged by means of the voltage source supplying the charging control voltage (VCC) and by means of the pullup resistor (215). Simultaneously, the timer (211) starts running and the digital sound processor (210) measures the charging voltage. Using the comparator (212), the charging voltage is compared to a predetermined threshold (VRef), which is here set to the value of the charging control voltage (VCC). When the charging voltage exceeds the threshold (VRef), the timer (211) stops running. The time interval determined by the timer (211) is then equal to the rise time of the sound processor antenna (201), which is the difference between the end time, at which the charging voltage exceeded the predetermined threshold, and the start time, at which the charging was started. Based on the determined rise time, the digital sound processor (210) then determines at least one state and/or property related to the cochlear implant system. Here, the digital sound processor (210) determines that the sound processor antenna (201) is connected to the sound processor unit. In addition, it determines a resonant frequency and an antenna type of the sound processor antenna (201) based on the determined rise time.

If no sound processor antenna was connected to the sound processor unit, the digital sound processor (210), more specifically the class D amplifier integrated into the digital sound processor (210), would only attempt to charge a sound processor antenna of the sound processor unit. Nevertheless, the method shown in FIG. 4 could still be performed, and the digital sound processor (210) in this case could determine, based on the determined rise time, that no sound processor antenna is connected to the sound processor unit.

Figure 6:
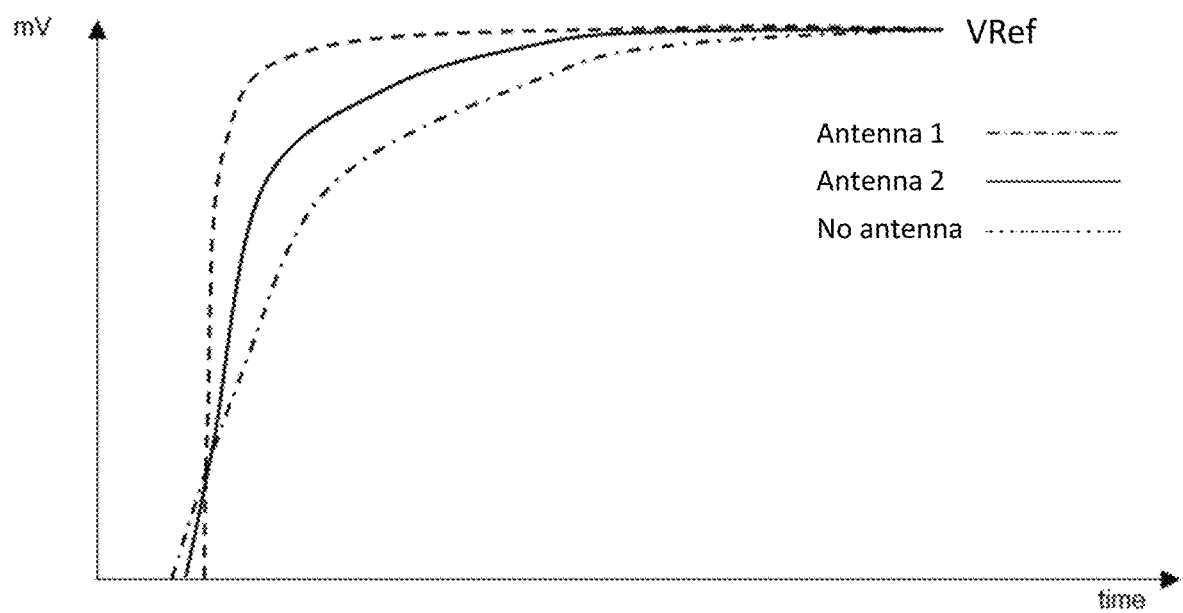
FIG. 6 shows exemplary charging voltage functions obtained by performing a method according to the third aspect.

With reference to FIG. 6, it is explained in the following how a resonant frequency and an antenna type of the sound processor antenna (201) are determined based on the determined rise time, or how it is determined, based on the determined rise time, that no sound processor antenna is connected to the sound processor unit. FIG. 6 shows exemplary charging voltage functions obtained by performing a method according to the third aspect. More specifically, a first charging voltage function obtained with a first type of sound processor antenna connected to a sound processor unit, a second charging voltage function obtained with a second type of sound processor antenna connected to a sound processor unit, and a third charging voltage function obtained with no sound processor antenna connected to a sound processor unit is shown. The individual charging voltage functions are referred to as "Antenna 1", "Antenna 2", and "No antenna" in FIG. 6. As the figure shows, the rise times corresponding to the different charging functions differ from each other: The charging voltage function corresponding to no sound processor antenna being connected has the smallest rise time and the threshold (VCC) is exceeded the earliest. Moreover, the charging voltage function corresponding to the first type of sound processor antenna has a longer rise time than the charging voltage function corresponding to the second type of sound processor antenna. Therefore, as FIG. 6 shows, the rise time is characteristic for whether a sound processor antenna is connected to the sound processor unit or not, and characteristic for the type of sound processor antenna. This correlation is used by the digital sound processor (210) of FIG. 6: It comprises a memory (216) with a database, in which different rise times are associated with different sound processor antenna types and their corresponding resonant frequency. The database also comprises the rise time corresponding to no sound processor antenna being connected to the sound processor unit. Then, by comparing the determined rise time with the rise times in the database, the digital sound processor (210) is able to determine, whether or not a sound processor antenna is connected to the sound processor unit, and to determine a resonant frequency and an antenna type of the sound processor antenna.

Determining whether or not a sound processor antenna is connected to the sound processor unit, and determining a resonant frequency of the sound processor antenna and a type of the sound processor antenna allows to optimise the operation of the cochlear implant system accordingly. For example, the sound processor unit or components of the sound processor unit may be deactivated if it is determined that no sound processor antenna is connected to the sound processor unit, or the sound processor unit or components of the sound processor unit may be activated or re-activated if it is determined that a sound processor antenna is connected to the sound processor unit. In addition, an inductive link between the sound processor antenna and an implant antenna of an implant unit of the cochlear implant system can be optimised with respect to the sound processor antenna if its type and/or resonant frequency are known.

The digital sound processor (210) shown in FIG. 5 performs the method shown in FIG. 4 during a booting process of the cochlear implant system, and after initiation by manual user input. This allows to determine whether or not a sound processor antenna is connected to the sound processor unit, and to determine at least one property related to the sound processor antenna, right after the cochlear implant system is switched on and starts its operation, and in case of an establishment or re-establishment of a connection between the sound processor unit and a sound processor antenna by a user.

After performing the method shown in FIG. 4 to determine the resonant frequency and antenna type of the sound processor antenna, the digital sound processor (210) of the sound processor unit uses the obtained resonant frequency to optimise the operation of the cochlear implant system, as will be explained below with reference to FIG. 2 and FIG. 5. At first, determining a resonant frequency of the sound processor antenna based on the determined antenna type would be conceivable. However, this is omitted here, since a resonant frequency of the sound processor antenna has already been determined based on the determined rise time. Instead, the resonant frequency of the sound processor antenna, which has been determined based on the determined rise time, is used as a carrier frequency for an inductive link (220) between the sound processor unit and an implant unit (cf. FIG. 2) of the cochlear implant system. For this purpose, the variable oscillator is used, which is integrated into the digital sound processor (210), as described above in the context of FIG. 2. The digital sound processor (210) controls the variable oscillator, which feeds the sound processor antenna (201), such that the determined resonant frequency of the sound processor antenna (201) is used as a carrier frequency for the inductive link (220). Furthermore, the digital sound processor (210) causes or triggers a method according to the second aspect to be performed, as explained above in the context of FIG. 2, in order to adjust the carrier frequency of the inductive link (220). Here, the lower and upper limit frequency for the method according to the second aspect are selected such that the lower and upper limit frequency form a frequency interval which includes the determined resonant frequency of the sound processor antenna (201). Thereby, optimised operation of the inductive link, for example with respect to power consumption or reliability of communication between the sound processor unit and the implant unit, is achieved. Overall, the operation of the cochlear implant system is optimised.

Figure 7:
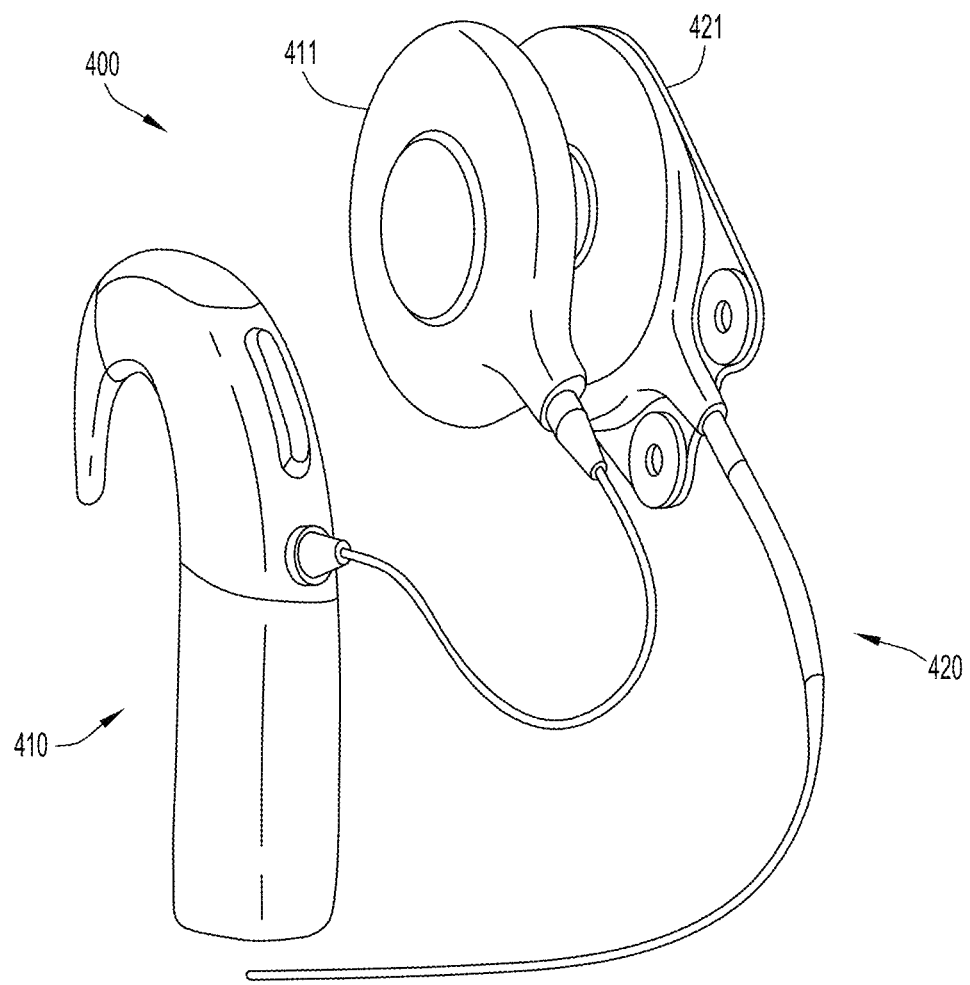
FIG. 7 shows a schematic illustration of a cochlear implant system with a sound processor unit according to the first, second and third aspect and an implant unit.

Referring now to FIG. 7, a schematic illustration of a cochlear implant system according to the first, second and third aspect is shown. The cochlear implant system (400) comprises an implant unit (420) with an implant antenna (421) and a sound processor unit (410) with a sound processor antenna (411). The sound processor unit (410) combines the features of a sound processor unit according to the first aspect, a sound processor unit according to the second aspect, and a sound processor unit according to the third aspect. Thereby, an improved cochlear implant system which combines the advantages of all three aspects is provided.

A computer program (product) comprising instructions which, when the program is executed by a computer, cause the computer to carry out (steps of) the methods described above, in the 'detailed description of embodiments' and in the claims is furthermore provided by the present application.

In an aspect, the functions may be stored on or encoded as one or more instructions or code on a tangible computer-readable medium. The computer readable medium includes computer storage media adapted to store a computer program comprising program codes, which when run on a processing system causes the data processing system to perform at least some (such as a majority or all) of the steps of the method described above, in the and in the claims.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

In an aspect, a data processing system comprising a processor adapted to execute the computer program for causing the processor to perform at least some (such as a majority or all) of the steps of the method described above and in the claims.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element, but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method are not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects. Reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A method comprising:
   generating, at an external portion of a medical device, electromagnetic waves, wherein a frequency of the electromagnetic waves is varied over time between a lower limit frequency and an upper limit frequency;
   measuring, as a function of the frequency of the generated electromagnetic waves, at least one parameter related to the medical device;
   selecting a frequency based on the measuring; and
   using the selected frequency as a carrier frequency for an inductive link between the external portion and an implantable portion of the medical device.

2. The method of claim 1, wherein generating the electromagnetic waves comprises:
   generating the electromagnetic waves using a variable oscillator.

3. The method of claim 1, wherein the at least one parameter is an amplitude of a response signal from an antenna of the implantable portion of the medical device.

4. The method of claim 1, wherein the at least one parameter is a parameter associated with a demodulated response signal from an antenna of the implantable portion of the medical device.

5. The method of claim 1, wherein the at least one parameter is a power consumption of the medical device.

6. The method of claim 5, wherein selecting the frequency comprises:
   selecting the frequency such that the power consumption of the medical device is minimized.

7. The method of claim 1, wherein measuring the at least one parameter comprises:
   measuring the at least one parameter using at least one analog-to-digital converter.

8. The method of claim 1, wherein measuring the at least one parameter comprises:
   measuring the at least one parameter using at least one demodulator.

9. The method of claim 1, wherein the generating the electromagnetic waves and the measuring the at least one parameter are performed simultaneously.

10. The method of claim 1, wherein the medical device is a hearing device.

11. A system, comprising:
an implantable portion; and
an external portion configured to:
  generate electromagnetic waves, wherein a frequency of the electromagnetic waves is varied over time between a lower limit frequency and an upper limit frequency;
  measure, as a function of the frequency of the generated electromagnetic waves, at least one parameter related to the system;
  select a frequency based on the measuring; and
  use the selected frequency as a carrier frequency for an inductive link between the external portion and the implantable portion.

12. The system of claim 11, wherein the external portion includes a variable oscillator configured to generate the electromagnetic waves.

13. The system of claim 11, wherein the at least one parameter is an amplitude of a response signal from an antenna of the implantable portion of the medical device.

14. The system of claim 11, wherein the at least one parameter is a parameter associated with a demodulated response signal from an antenna of the implantable portion of the medical device.

15. The system of claim 11, wherein the at least one parameter is a power consumption of at least one of the implantable portion or the external portion.

16. The system of claim 15, wherein, when selecting the frequency, the external portion is further configured to select the frequency such that the power consumption of the at least one of the implantable portion or the external portion is minimized.

17. The system of claim 11, wherein, when measuring the at least one parameter, the external portion is configured to measure the at least one parameter using at least one analog-to-digital converter.

18. The system of claim 11, wherein, when measuring the at least one parameter, the external portion is configured to measure the at least one parameter using at least one demodulator.

19. The system of claim 11, wherein the external portion is configured to generate the electromagnetic waves and measure the at least one parameter simultaneously.

20. The system of claim 11, wherein the external portion is a sound processing unit of a cochlear implant system.

* * * * *